United States Patent
Bradley et al.

(10) Patent No.: US 11,634,461 B2
(45) Date of Patent: Apr. 25, 2023

(54) BARLEY PROTEIN PRODUCTION PROCESS

(71) Applicant: Montana Microbial Products, LLC, Missoula, MT (US)

(72) Inventors: Clifford A. Bradley, Missoula, MT (US); Robert D. Kearns, Melrose, MT (US)

(73) Assignee: Montana Microbial Products, LLC, Missoula, MT (US)

( * ) Notice: Subject to any disclaimer, the term of this patent is extended or adjusted under 35 U.S.C. 154(b) by 0 days.

(21) Appl. No.: 17/170,716

(22) Filed: Feb. 8, 2021

(65) Prior Publication Data

US 2021/0284700 A1 Sep. 16, 2021

Related U.S. Application Data

(63) Continuation of application No. PCT/US2021/016761, filed on Feb. 5, 2021.

(60) Provisional application No. 62/959,481, filed on Mar. 13, 2020, provisional application No. 62/989,483, filed on Mar. 13, 2020.

(51) Int. Cl.
*C07K 14/415* (2006.01)
*C12P 19/02* (2006.01)
*C12P 19/14* (2006.01)

(52) U.S. Cl.
CPC ............ *C07K 14/415* (2013.01); *C12P 19/02* (2013.01); *C12P 19/14* (2013.01); *C12Y 302/01001* (2013.01); *C12Y 302/01004* (2013.01); *C12Y 302/01041* (2013.01)

(58) Field of Classification Search
CPC ........ C12P 19/14; C12P 19/02; C07K 14/415; C12Y 302/01001; C12Y 302/01004; C12Y 302/01041
See application file for complete search history.

(56) References Cited

U.S. PATENT DOCUMENTS

| | | | |
|---|---|---|---|
| 3,958,015 A | 5/1976 | Gay | |
| 4,311,714 A | 1/1982 | Goering et al. | |
| 4,990,344 A | 2/1991 | Euber et al. | |
| 8,481,677 B2 | 7/2013 | Barrows et al. | |
| 9,226,515 B2 * | 1/2016 | Slabbekoorn | A23K 50/30 |
| 9,644,228 B2 * | 5/2017 | Barrows | C12P 21/00 |
| 2003/0180415 A1 | 9/2003 | Stiefel et al. | |
| 2007/0092629 A1 | 4/2007 | Scanlin et al. | |
| 2007/0172914 A1 | 7/2007 | Slabbekoorn et al. | |
| 2008/0279983 A1 | 11/2008 | Lohrmann et al. | |
| 2013/0274443 A1 | 10/2013 | Barrows et al. | |
| 2019/0200640 A1 | 7/2019 | Gil-Martinez et al. | |

FOREIGN PATENT DOCUMENTS

| | | |
|---|---|---|
| AU | 2009236220 B2 | 10/2014 |
| AU | 2015200127 | 2/2017 |
| CA | 2721617 C | 6/2016 |
| EP | 2276352 | 1/2020 |
| JP | 57446614 B2 | 7/2015 |
| JP | 2015128429 A | 7/2015 |
| MX | 314131 | 7/2014 |
| MX | 361478 B | 12/2018 |
| WO | 2005082155 A2 | 9/2005 |
| WO | 2006119206 A2 | 11/2006 |
| WO | 2009129320 A2 | 10/2009 |
| WO | 2009129320 A3 | 12/2009 |
| WO | 2015057517 A1 | 4/2015 |

* cited by examiner

*Primary Examiner* — Ganapathirama Raghu
(74) *Attorney, Agent, or Firm* — Sarah J. Rhoades

(57) ABSTRACT

A process to produce a protein concentrate from grain, specifically barley protein concentrate (BPC) through mechanical and biochemical intervention while producing multiple sugar streams as co-products. The resulting BPC preferably contains 54%-95% protein derived exclusively from the enzymatically processed barley and has a pH>5.0. The BPC may contain approximately 10% oil, less than 5% crude fiber, less than 1% residual glucose, and less than 0.5% phytic acid. The BPC contains no ethanol, organic acid, fermentation products, or microbial cells or cell mass. No fermentation occurs in the production of the BPC. The BPC has unique applications in formulations for aquaculture or livestock feed, and other pet food as well as for food formulations intended for human consumption. The sugar co-products, including glucose, have applications in industry and science and are particularly suitable for use as feedstocks for fermentation processes, livestock feeds, or biochemical conversion processes.

16 Claims, 9 Drawing Sheets

BARLEY PROTEIN PRODUCTION PROCESS

CROSS-REFERENCE TO RELATED APPLICATIONS

This patent application claims priority under 35 U.S.C. § 119(e) to U.S. Patent Application Ser. No. 62/989,483, entitled "Barley Protein Concentrate, Production Process, Composition and Uses", and filed on Mar. 13, 2020. This patent application also claims priority under 35 U.S.C. § 119(e) to U.S. Patent Application Ser. No. 62/989,481, entitled "Barley Protein Concentrate, Composition and Uses", and filed on Mar. 13, 2020. The entire disclosures of those provisional patent applications are hereby incorporated by reference.

STATEMENT REGARDING FEDERALLY SPONSORED RESEARCH OR DEVELOPMENT

Not applicable.

THE NAMES OF THE PARTIES TO A JOINT RESEARCH AGREEMENT

Not applicable.

INCORPORATION-BY-REFERENCE OF MATERIAL SUBMITTED ON A COMPACT DISC

Not applicable.

BACKGROUND OF THE INVENTION

1. Field of the Invention

This invention relates to the production of high-protein concentrate from plant materials using an enzymatic process without the use of harsh solvents or chemicals. The protein concentrate of this invention does not have the undesirable characteristics of fermentation to ethanol which requires additional distillation steps or which limits the use of other plant derived proteins as an ingredient in aquaculture feeds, livestock and poultry feeds, pet food and human foods. The invention more particularly relates to processes for creating those plant-based protein concentrates with optimum protein yield—while extracting and utilizing sugar co-products like glucose and minimizing undesirable compounds. The protein concentrate of this invention has broad utility as a protein ingredient in aquaculture feeds, livestock and poultry feeds, pet foods and human food.

2. Description of Related Art

Plant based protein concentrates produced from oil seeds—such as soybeans or canola, peas, grains such as wheat and corn, distillers' grains (from corn based ethanol production), nuts, etc.—are widely used as a protein ingredient in aquaculture feeds, livestock feeds, pet foods and in human foods. Use of plant derived protein concentrates to produce meat substitutes for human food is expanding rapidly. There is a critical need to replace animal derived proteins in aquaculture feeds, livestock feeds, pet food and human food with high quality plant proteins which meet nutritional requirements and which have suitable characteristics for flavor, odor and physical structure of final products. Protein concentrations in plant protein concentrates generally range from 55% to 70% (soy derived proteins are classified in three categories "soy meal" is 48% protein, "soy protein concentrates" are 55% to 70%, and "soy protein isolates" are 70% to 90%).

Currently available plant based protein concentrates have characteristics or compositions (such as ethanol, excess glucose, and allergens) which restrict and limit the quantity or concentration that can be incorporated into finished animal feed or human food products. Those characteristics or compositions further limit use of those protein concentrates in certain applications or raise human health concerns.

Corn gluten meal produced from corn wet milling processes imparts undesirable yellow color to final products, for example to meat substitutes or flesh color of farmed fish.

Wheat gluten meal produced from water washing wheat flour to remove starch granules contains high concentration wheat gluten, an issue in human food use for people with gluten intolerance.

Soy is one of the 8 most common human food allergens and also contains phytoestrogens which have raised health concerns. Nut derived protein concentrates also raise human allergy concerns Soy protein concentrates contain "antinutritional factors" which limit inclusion rates in aquaculture feeds and have low protein availability compared with animal derived proteins. For example, in aquaculture feeds for carnivorous fish such as trout and salmon, the amount of soy protein concentrate in final feed is limited to inclusion rates of no more than about 15%. A 15% inclusion rate means that in 100 pounds of finished feed there would be 15 pounds of the soy protein concentrate. At higher inclusion rates soy causes adverse effects to the digestive system of farmed fish.

Soy proteins are produced from soybeans treated with hexane or other solvents to remove oil. Pea proteins have health issues when used in pet food. Both soy and pea protein concentrates have bitter flavors which affect use in animal and human food. High fiber content limits use of distillers' grains.

Mechanical fractionation using density separation, air classifications systems avoid chemical processes however protein concentration in final products are generally less than 50%, which limits use. Soy protein concentrates are available in large quantities globally, yet other protein concentrates are produced in limited quantities that preclude large scale applications.

Environmental concerns also limit consumer acceptance of some protein concentrates, especially soy proteins produced from genetically modified soybeans and from expanded production at the expense of the Amazon forests.

Barley has not been used as a feedstock for producing protein concentrates except as described in U.S. Pat. Nos. 8,481,677 and 9,644,228, 8,481,677 claimed the creation of a protein concentrate by an enzymatic, and fermentation process with low temperature drying. U.S. Pat. No. 9,644,228 claimed the creation of a palatable protein requiring fermentation and then an active distillation step after the final separation of the protein solid from the liquids. The process described in these patents separates protein containing solids after fermentation. Those patents include process steps to distill ethanol created by the added organisms such as fungi, bacteria or yeast used to ferment the solubilized grains and oil seeds (including barley) after the final separation of solids and liquids, resulting in the recovery and drying of solids to produce protein concentrate. For the process in those patents the protein concentrate is a direct product of both solubilization and fermentation of carbohydrates in the grain or oilseed. Additionally, the protein concentrate contains more than an insignificant volume of the cell mass of the fermentation organism, as well as fermentation products such as organic acids and the insoluble protein from the grain or oilseed that were not removed in the mandatory distillation step.

The protein concentrate and processes of U.S. Pat. Nos. 8,481,677 and 9,644,228 require integration of fermentation organisms and a fermentation step producing ethanol and requiring culturing of microbes in the liquids to provide cell mass. Therefore, industrial distillation is a mandatory part of those processes. Because the process includes fermentation, the protein concentrate of U.S. Pat. Nos. 8,481,677 and 9,644,228 contains residual ethanol, other fermentation products, residual sugars, cells of the fermentation organisms, and cell mass recovered in the solids. The pH of the protein concentrate from the process of U.S. Pat. Nos. 8,481,677 and 9,644,228 is about 4.0 to 4.2. The protein concentrate in the prior inventions include cell mass of fermentation organisms and have lower protein concentration and increased amounts of residual glucose, other soluble sugars and soluble minerals compared with the protein concentrate of the present invention.

There is a need for a high quality, plant based protein concentrate with composition and characteristics to overcome limitations of current plant proteins and processes for producing plant protein concentrates.

BRIEF SUMMARY OF THE INVENTION

A process for producing barley protein concentrate and a plurality of sugar co-products from barley flour, the process comprising: a solubilization step, a liquefaction step, a saccharification step, at least one separation step, and a drying step, wherein the process results in the production of barley protein concentrate and at least one liquid sugar stream harvested from the process as a co-product. In the preferred embodiment, a purification step, also called a concentration step, will follow the initial separation step. The purification step may include any number of techniques used for purifying a wet solid, such as a wash step, a dilution step, or a membrane or other filtration step. In this preferred embodiment of the process, the purification step is followed by a second separation step. From this second separation step, a sugar stream of glucose is recovered as liquid. In some embodiments, the solubilization step, liquefaction step, and saccharification step occur in separate vessels with reaction parameters optimized for each step with transfer of material between vessels. In some embodiments, the liquefaction step and the saccharification step occur in one vessel, the slurry does not necessarily physically move if the reaction parameters can otherwise be achieved. In fact, in some circumstances, the solubilization step, the liquefaction step and the saccharification step occur in one receptacle or tank.

The barley flour used in the first step of the process is procured from dehulled and ground barley. In the preferred implementation, solubilization occurs at a temperature between 55° C. and 75° C., liquefaction occurs at a temperature between 75° C. to 85° C., and saccharification occurs at a temperature between 55° C. to 70° C., preferably greater than 60° C. to inhibit bacterial growth.

Process enzymes could be added to the any or all of the solubilization step, the liquefaction step and the saccharification step but in the preferred implementations of the process enzymes are added to the solubilization step and the saccharification step. Because the process may occur in one container, the enzymatic action may occur throughout the initial stages of the process.

The glucose coproduct is recovered from the process as a liquid stream of sugars after the various separation steps. Additionally, a liquid stream of short chain dextrins may be harvested from the process before the saccharification step.

In one embodiment, the invention produces a protein concentrate from barley grain at a protein concentration of greater than 54% of dry weight composition. The produced barley protein concentrate (BPC) is preferably 65% protein. In some refinements of the process upwards of 70% protein concentration will be achieved. Additional refinements may render the protein concentrate a nearly pure protein. All of the protein is derived from the barley used in the process. The BPC of the present invention contains low crude fiber, low residual glucose, low phytic acid, and have a mildly acidic to neutral pH. More specifically, and in a preferred embodiment, by way of example and not necessarily by way of limitation, the BPC contains 8% to 12% oil, less than 5% crude fiber, less than 1% residual glucose, less than 0.5% phytic acid, and has a pH greater than 5.0. The BPC of the preferred embodiment contains no ethanol, organic acids, residual fermentation products, yeast cells, fungi or other microbial cell mass.

The BPC of the present invention will have applications in formulations for aquaculture feed and other pet food or livestock feed. The preferred embodiment of the BPC will also have unique applications for food formulations intended for human consumption.

In the present invention the term protein concentrate refers to a plant derived protein containing 55% to 95% protein. The protein concentrate of this invention produced from barley is superior in composition and utility when compared to protein concentrates produced from other grains and oil seeds. It is an objective of the invention that a protein concentrate, glucose co-product, and residual barley hulls are produced from barley. It is a further objective of the present invention that the process for producing the protein concentrate and glucose uses a unique enzymatic process without the use of fermentation, harsh solvents or chemicals. It is still a further objective of the present invention that the resulting protein concentrate has superior composition and properties for use as a protein ingredient in aquaculture feeds, livestock and poultry feeds, pet foods and human food. It is still a further objective of the present invention that the glucose co-product has unique characteristics to make it desirable for many complementary, industrial uses.

The protein concentrate and the process of this invention differ substantially from the protein concentrate and processes of U.S. Pat. Nos. 8,481,677 and 9,644,228. No fermentation organisms, fermentation, or distillation steps are integrated into the present inventive process. The process of creating the protein described and claimed in this invention uses no integral fermentation organism, no fermenting slurry, no fermentation or distillation steps, and no culturing of microbes in the liquids fraction to provide cell mass. The protein concentrate of this invention contains no ethanol or other fermentation products, minimal residual sugars, no cells of fermentation organisms and no cell mass recovered in solids fraction. The pH of the protein concentrate of this invention is about 5.4 (5.2 to 5.6) compared with the pH of the protein concentrate of about 4.0 to 4.2 from the process of U.S. Pat. Nos. 8,481,677 and 9,644,228. In the process of this invention, a solids fraction containing protein is recovered without the addition of a fermentation organism or microbe cultured for cell mass. Fermentation may be used external to the BPC process and downstream of the liquids fraction separation as a means to monetize the extracted glucose; however, the glucose recovered as a co-product during the liquid separation is recovered at such high percentage yields that yeast cells are exposed to high osmotic stress, which can negatively impact the fermentation to ethanol. The process of this invention incorporates a "purification step," also called an additional concentration step, of the recovered solids fraction prior to drying, thereby producing a protein concentrate with higher protein concentration and reduced residual glucose, as well as reduced amounts of other soluble sugars and soluble minerals.

The BPC of the present invention is produced according to a unique process, which in one exemplary embodiment comprises the steps of:

a) Dehulling and grinding the barley grain to produce a barley flour;

b) Mixing the flour with hot water at a temperature of 55 to 75° C. to form a slurry with 20 to 40% weight per volume flour, adding thermotolerant alpha amylase (such as EC 3.2.1.1, 1,4-alpha-D-glucan glucanohydrolase) and beta glucanase (such as EC 3.2.1.6, 3-beta-D-glucan 3(4)-glucanohydrolase), and holding the modified slurry containing the enzymes for a reaction time of 20 minutes to 45 minutes in a solubilization step in a first reaction tank;

c) Transferring the slurry to a liquefaction step in a second reaction tank and increasing the slurry temperature to 75 to 85° C. for a reaction time of 2 to 6 hours. In some implementations, a liquid stream of short chain dextrins may optionally be separated from the wet solids prior to the slurry being transferred to the next stages of the process;

d) Cooling the slurry to 55° C. to 70° C. while or after transferring the slurry to the saccharification step in a third reaction tank and introducing additional glucoamylase enzyme preparations containing glucoamylase and debranching activities (such as EC 3.2.1.3 1,4-alpha-D-Glucan glucohydrolase and EC 3.2.1.41 Alpha-dextrin endo-1,6-alpha-glucosidase), cellulase preparations containing endocellulases (such as EC 3.2.1.4 endo-1,4-beta-D-glucanase), exocellulases (such as EC 3.2.1.91 cellulose 1,4-beta-cellobiosidase), and beta glucosidase (such as EC 3.2.1.21, β-D-glucoside glucohydrolase), hemicellulases containing mixtures of xylanases (such as EC 3.2.1.8), β-mannanase (such as EC 3.2.1.78), arabinofuranosidase (such as EC 3.2.1.55), β-xylosidase (such as EC 3.2.1.37, and phytase (such as EC 3.1.3.26, EC 3.1.3.8) activities for a time of 4 to 14 hours;

e) Separating the slurry into wet solids fraction containing protein and a primary liquids fraction containing 18% to 30% glucose;

f) Further purifying the protein contained in the wet solids fraction from step (e) and separating purified wet protein solids containing protein and a secondary liquids fraction, the secondary liquid fraction containing about 3 to 6% glucose, plus lesser concentrations of other soluble sugars and minerals;

g) Drying the solids fraction containing purified protein at a temperature and under conditions which do not damage or adversely affect protein, thereby producing a protein concentrate containing greater than 54% protein;

h) Recovering the primary liquid fraction containing an enriched sugar stream of glucose of step (e) for use as a feedstock for industrial fermentation processes; or i) Processing the glucose-containing, primary liquids fraction of step (h) to a form suitable for supplementation into animal feeds or fermentation processes or biochemical conversions;

j) Recovering the glucose-containing, secondary liquids fraction from step (0; and processing that secondary liquids fraction containing glucose as a feedstock for organic acid production, other fermentation products or microbial cell mass, or recycling the secondary liquids fraction as water to form the slurry in step (b) or combining the secondary liquids fraction with the primary liquids fraction of step (e) to further enrich the sugar stream.

Step (i) is optional depending on how the glucose will be used and whether further processing is necessary for that use. Steps (h) and (j) do not necessarily need to happen in sequence after step (g) but may be commenced at various timing intervals and repeated as necessary. In some embodiments, step (f) can occur simultaneously with step (e). Those, and other embodiments, can eliminate step (j). Additional modifications of the above steps may be permissible so long as the final protein isolate has a high concentration of barley protein and low concentrations of residual glucose or other sugars.

In practice, barley flour is mixed with water in a first reaction tank also called a solubilization tank to form a slurry at 20% to 40% solids content at a water temperature which gelatinizes starch in the barley. After the addition of alpha amylase and beta glucan hydrolytic enzymes, the resulting slurry is stirred in the first tank and allowed to react for a period of time until the viscosity is substantially reduced. The mixed slurry of solid and soluble matter is then pumped through a hydroheater, heat exchanger, or other device for increasing temperature and which may also introduce steam. In the ideal process, the heat is recycled in the process, such as through the use of a heat exchanger, to conserve energy in other portions of the system. The slurry's temperature is increased as the slurry is moved to a second tank. The second tank, also called a liquefaction tank, is kept hotter than the prior tank and the mixture is allowed to react at temperature for 2-6 hours, while the thermotolerant enzymes are hydrolyzing the carbohydrates in the barley slurry. The slurry is then cooled, again with the objective to recycle the energy such as through the use of a heat exchanger, and, in a third tank, also called a saccharification tank, additional enzymes are added to further hydrolyze the carbohydrates. Once again, the ideal process, will use heat exchangers to pull off or add heat and recycle the energy from other portions of the system. The resulting 10-15 percent solids mixture leaves tank three and enters the continuous flow centrifuge for the first stage of separating the sugar-enriched liquids fraction from the solids fraction. The glucose co-product is removed in the first liquids fraction also referred to as a primary liquids fraction, leaving a 30% to 40% wet solid. Additional warm water is added to the wet solid and the mixture is separated a second time. In one embodiment, the wet solid is passed through a continuous flow, rotary screen with countercurrent flow of water. In another embodiment, additional centrifuge cycles will separate liquids and solids. Other equipment known in the art may be used to separate liquids and solids in steps (e) and (f). Step (f) further purifies the barley protein concentrate by removing additional glucose and other soluble impurities in the secondary liquids fraction, leaving the highest quality protein in the solids fraction to be dried and prepared for use or consumption. With the highest and best use equipment, the entire process including mixing, titrating enzymes, retaining, heating, cooling, separating, purifying, and drying could be accomplished with continuous flow. Flour would continuously flow into the system at tank 1 with enzymes metered in at predetermined amounts, and the slurry continuously flowed through the remainder of the process until a final solids fraction was recovered and dried. Reaction time at each step is set by controlling by flow rate through the process and process tank volume. The final glucose concentration in the barley protein concentrate is highly desirable at less than 1%.

In the preferred embodiment, the primary liquid glucose containing fraction of step (e) can be used in fermentations without further processing or is further processed to a form suitable for use as supplement for animal feeds or for use as feedstocks for fermentation, industrial processes, or biochemical conversion. Industrial processes include fermentation processes for producing antibiotics, ethanol, enzymes, and other end-use products requiring a glucose feedstock, as well as biochemical conversion to polyols and other higher value compounds.

Furthermore, in the preferred process of creating the present invention the secondary glucose containing liquid fraction from step (f) is recycled as make up water in forming the slurry in step (b). The above identified process can be further utilized such that the secondary glucose containing liquid fraction from step (f) is used as fermentation feedstock or the secondary glucose containing liquid fraction from step (f) can be combined with the liquid fractions of step (e) to further supplement the primary liquids fraction. By-products of the barley hulls from step (a) are used for livestock feed, fiber or fuel. In certain instances, it may be desirable to purchase barley that is previously dehulled or of a specific variety with little or no hulls. It is also possible to purchase prepared barley flour. In those instances, step (a) could be shortened or eliminated. In the preferred implementation of the process, the above steps will be operated as a continuous process but could alternatively be implemented as a batch process.

The foregoing has outlined, in general, the physical aspects of the invention and is to serve as an aid to better understanding the more complete detailed description which is to follow. In reference to such, there is to be a clear understanding that the present invention is not limited to the method or detail of construction, fabrication, material, or application of use described and illustrated herein. Any other variation of fabrication, use, or application should be considered apparent as an alternative embodiment of the present invention.

DETAILED DESCRIPTION OF THE INVENTION

Figure 1:
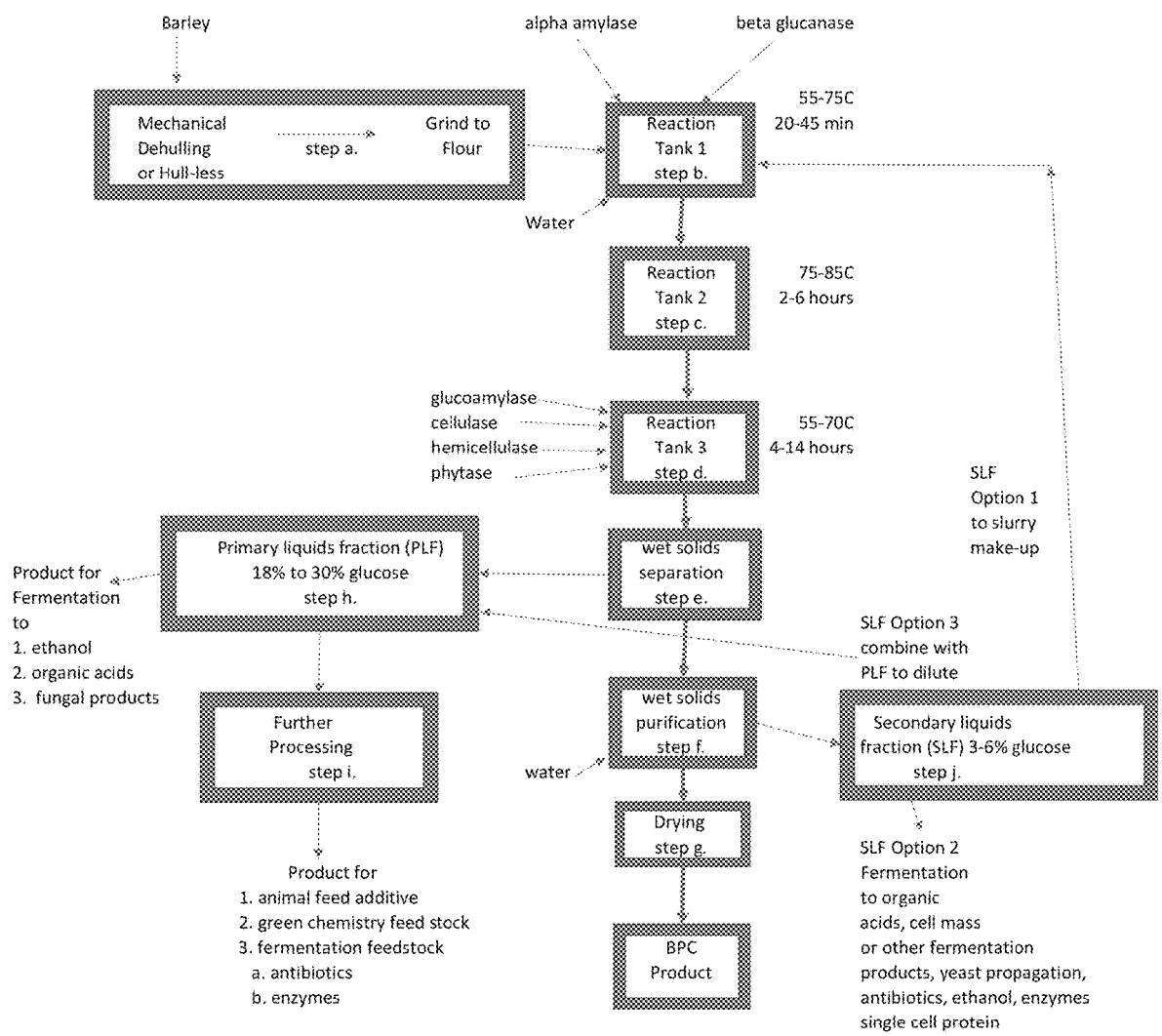
FIG. 1 illustrates a process flow according to the present invention used to create the claimed barley protein concentrate and also illustrates suggested byproduct isolates and uses.

The invention comprises a barley protein concentrate (BPC) produced from barley and the enzymatic process used to produce the protein concentrate. The BPC of the present invention created by the preferred processes described herein is a unique, original, and unexpected source of high quality protein which stands apart from other grains and oilseed used for similar purposes. The BPC of the present invention is superior in composition and characteristics to other plant derived proteins for uses in aquaculture feeds, livestock feed, poultry feed, pet foods, and human foods. A second aspect of the present invention is the process for manufacturing the protein concentrate, starting with barley at 10% to 15% protein content and achieving a product in most cases ranging from 55% to 70% protein by using an enzymatic process without fermentation and without the use of solvents or harsh chemicals. A third aspect of the present invention is production of a valuable glucose-containing process stream with multiple applications. A fourth aspect of the present invention is production of a barley hull-containing process stream with multiple applications.

The barley protein concentrate (BPC) created according to the preferred processes of the present invention will result in a BPC that is preferably 65% protein (but ranges from 55% to 70% and, with further processing, almost pure protein concentrate at 95%) all of which is derived from the barley used in the process. The BPC produced according to the processes of the present invention contains less than five percent (5%) crude fiber, less than one percent (1%) residual soluble sugars such as glucose and no residual organic acids or other fermentation products within the BPC. Final pH of the present invention BPC is about 5.4 (ranges may include 5.0 to 5.6). The low residual sugars of the present invention BPC are a particular advantage in aquaculture feeds for carnivorous fish such as salmonids where excess glucose adversely affects fish health; and for inclusion in human foods where glucose raises concerns with diabetes. The pH in the present invention BPC is less acidic than proteins produced from typical fermentation processes which result in more acidic proteins, in the range of 4.0 to 4.5, unless pH is adjusted in additional process steps. The higher pH of the present invention is an advantage in that it improves palatability in aquaculture and livestock feeds and allows the BPC greater versatility for incorporation as a protein concentrate into human food formulations. The BPC created through the present invention contains about 10% oil which provides additional energy when used in feeds. The process also converts indigestible phytic acid to digestible phosphate which is present in the resulting BPC. The unique BPC created through the processes detailed herein does not contain phytoestrogens or common human allergens, it does not contain antinutritional factors as found in soy, and it does not contain microbial cell mass which might impact quality, allergenicity or acceptability of the barley protein concentrate in pet feeds or human food.

In studies using the BPC of the present invention as a protein ingredient in aquaculture feeds, the protein digestibility was greater than soy protein and equal to or greater than animal derived proteins such as fishmeal. In aquaculture feeds, BPC can be used at much higher inclusion rates compared to other plant proteins, up to 40% in some studies and 30% in a large scale trial in trout. BPC has been shown to have advantageous physical characteristics for producing pelleted feeds used in aquaculture and livestock feeds.

The BPC of the present invention has a bland flavor with minimal odor. It does not have the bitter flavor of other plant proteins, enabling use at higher concentrations and with greater versatility in pet foods and in human foods. The absence of phytoestrogens, allergens and microbial cell mass in the present invention's BPC alleviates consumer concerns when used as an ingredient in human foods.

The BPC claimed herein and created according to the present inventive processes, also meets criteria for health, sustainability and environmental impact set out by various governmental and consumer organizations (for example, the Aquaculture Stewardship Council). Unlike soy and canola, barley used in the present invention's BPC process has not been genetically modified, meeting consumer preferences in human food uses such as plant based meat substitutes. Barley used in the present invention BPC process is grown primarily as a rotation crop on land already in production; thus, BPC production according to the present invention will not require creation of new farmland from forest or native grasslands. Barley used to make BPC according to the present inventive process does not compete with most other food crops. Advantageously, most barley including the barley used in the process disclosed herein to create BPC is grown without irrigation in cold and dry climates unsuited for most other crops. Barley, including the barley used for the present invention BPC, is a short season, low input crop which requires less fertilizer and pesticides than other grains.

Process

One example of a BPC process flow diagram for producing BPC is shown in FIG. 1. BPC of this invention is produced using an enzymatic process which hydrolyzes the starch, beta glucans and fiber to enriched, soluble sugars, primarily glucose. Using a centrifuge (or other means such as filtration using a filter press or mash filter, or membrane separation for separating solids and liquid fractions), a solids fraction containing insoluble protein is separated from a primary liquids fraction containing soluble sugars. The solids fraction is further processed in a purification step and dried to form the BPC product. The purification step produces a secondary liquids fraction. The BPC product is a dry solid such as in the form of powder with ideally 65% (but as little as 55% or as much as 95%) protein dry matter basis with approximately 10% oil, less than 5% crude fiber, less than 1% residual glucose, and a final pH of 5.4 (5.2 to 5.6). The first and second glucose co-products produced through this process are highly useful in industry applications. The first glucose product, called the primary liquids fraction is a water solution containing 18% to 30% glucose, typically 23% where the glucose accounts for more than 95% of the total soluble sugars. The solution contains soluble protein, trace amounts of pentose sugars from hemicellulose hydrolysis and trace amounts of soluble dextrins with a degree of polymerization of 2 to 4 glucose residues. The second glucose product, called the secondary liquids fraction, contains about 3% to 6% glucose plus trace amounts of other soluble sugars, soluble protein, and soluble dextrins.

The present invention BPC can be produced from barley grain of any variety and grown under any conditions. The ideal protein will be recovered from grain that meets basic specifications for feed barley, more particularly, anything above barley grain meeting specifications for number 2 feed barley in the U.S. is most suitable as feedstock for the process to create the BPC of the present invention.

Enzymatic hydrolysis of starch is a common agricultural industrial process such as used in the production of ethanol from corn. However, the preferred enzymatic treatment used to produce the present invention BPC varies substantially from conventional enzymatic hydrolysis of corn or other grains. Typical grain processes use two commercially available enzyme preparations, alpha amylase and glucoamylase, to convert starch to glucose for fermentation to ethanol or as feedstock for other fermentation of biochemically derived products. Enzymes and processes for enzymatic hydrolysis of cellulose in plant materials have also been developed. The BPC of the present invention and the process by which it is made are unique in that starch hydrolytic enzymes are combined with beta glucanases to hydrolyze beta glucan and with cellulose and hemicellulose hydrolytic enzymes, all in a process to produce a plant protein concentrate. In some embodiments of the present inventive process, a phytase is added to convert phytic acid in the barley to digestible phosphate. The preferred process also concentrates and recovers the oil in barley in the final BPC product. Unlike the two amylases used in conventional starch conversion processes, the preferred process by which the BPC is produced uses 5 enzymes with enzyme loading rates, temperature and reaction times that vary substantially from conventional processes to produce protein concentrate with the desired characteristics. This can be accomplished by either a batch or a continuous flow process. Protein products from conventional enzymatic processes do not meet the characteristics and quality of the present invention's BPC as a protein concentrate. For example, corn dry milling and enzymatic hydrolysis for ethanol production produces distillers' grains as a co-product. Distillers' grains are typically about 25% to 30% protein with fiber content greater than 20%. Corn distillers' grains and other plant derived proteins produced from enzymatic processes do not have high enough protein content and low enough fiber content to function as protein concentrates of this invention.

Example—FIG. 1

As illustrated in FIG. 1, the following is an example of the process and ultimate production of the BPC and co-products:

Barley grain is mechanically dehulled, then ground to a coarse flour using standard grain processing equipment, step (a). In certain instances, it may be desirable to purchase barley that is previously dehulled or of a specific variety with little or no hulls. It is also possible to purchase prepared barley flour. In those instances, step (a) could be shortened or eliminated.

In a first reaction tank, flour is mixed with water at a temperature of 55° C.-75° C. to form a slurry, and thermotolerant alpha amylase and beta glucanase are added to form a modified slurry with 20% to 40% or more solids content and held with a retention time of 20 to 45 minutes, step (b). The modified slurry is moved to a second reaction tank and further heated to 75° C. to 85° C. where it is held for 2 to 6 hours, step (c). Holding the reactions at high temperatures ensures complete gelatinization of starch granules and helps reduce the likelihood of contamination by microbes. Then the slurry is transferred to a third reaction tank and cooled to 55° C. to 70° C. Glucoamylase, cellulase, hemicellulase and phytase enzymes are added to the modified slurry in the third reaction tank and held at 55° C. to 70° C. for 4 to 14 hours, step (d). Enzymes suitable for the process include thermotolerant alpha amylase, thermotolerant beta glucanase, glucoamylase, phytase, cellulase and hemicellulase preparations from DuPont corporation. Enzyme preparations with similar activities and temperature ranges from other suppliers, for example Novozymes are also suitable for the process of the present invention. While the elimination of glucoamylase could result in a barley protein concentrate, the primary liquids fraction or the secondary liquids fraction would contain primarily soluble dextrins. Soluble dextrins could have applications in fermentation or industrial processes or could be converted to glucose with further enzymatic treatment to convert dextrins to glucose.

With continuing reference to FIG. 1, step (e) represents enzymatically treated slurry being transferred to a centrifuge to separate solids containing protein from the primary liquids fraction containing enriched, soluble sugars and water. After the initial separation step (e), wet solids from the centrifuge are mixed with 1 to 3 volumes of water then centrifuged again as a "purification" step to separate solids containing protein from a secondary liquids fraction to remove residual soluble sugars from the solids protein containing fraction, step (f). Recovered solids are dried in step (g). In one embodiment, the drying is done using a continuous flow microwave dryer to form the final BPC product.

In the process represented in FIG. 1, the step (e) separation of the solids fraction containing protein and the primary liquids fraction is done using a centrifuge or rotary disc filter system, while the purification in step (f) can be accomplished by using a mix tank or a paddle mixer operated under continuous flow mixing water and wet solids and using a centrifuge or rotary disc filter to separate purified solids and secondary liquids fraction. These steps (e) and (f) can also be accomplished by these or combinations of similar methods known in the industry, such as, for example, by filtration using a filter press or mash filter, or by membrane separation or other device for separating liquids and solids. In FIG. 1, drying is accomplished using a continuous flow microwave dryer. Other various drying mechanisms can be readily implemented. Any industrial drying equipment must use temperatures and residence time in dryer which do not denature or adversely affect the palatability, flavor or digestibility of the protein. It is important that the temperature of the protein does not exceed 85° C. during drying.

The inventive process generates enriched sugar streams comprising a primary liquids fraction and a secondary liquids fraction. Each fraction contains soluble sugars. More than 95% of that soluble sugar is glucose. Supernatant, primary liquids fraction from the first solid and liquid separation in step (e) contains about 20% glucose concentrations but glucose is recovered in the range of 18% to 30% concentration. Co-product streams seeking to use the glucose for fermentation, will need to dilute these high concentration yields before they can be useful to yeast for fermentation. The secondary liquids fraction from the second solids and liquid separation, in the purification step (f) contains about 4% glucose (3% to 6%). Glucose streams from the primary liquids fraction and from the secondary liquids fraction are each valuable co-products with multiple potential applications.

Figure 2:
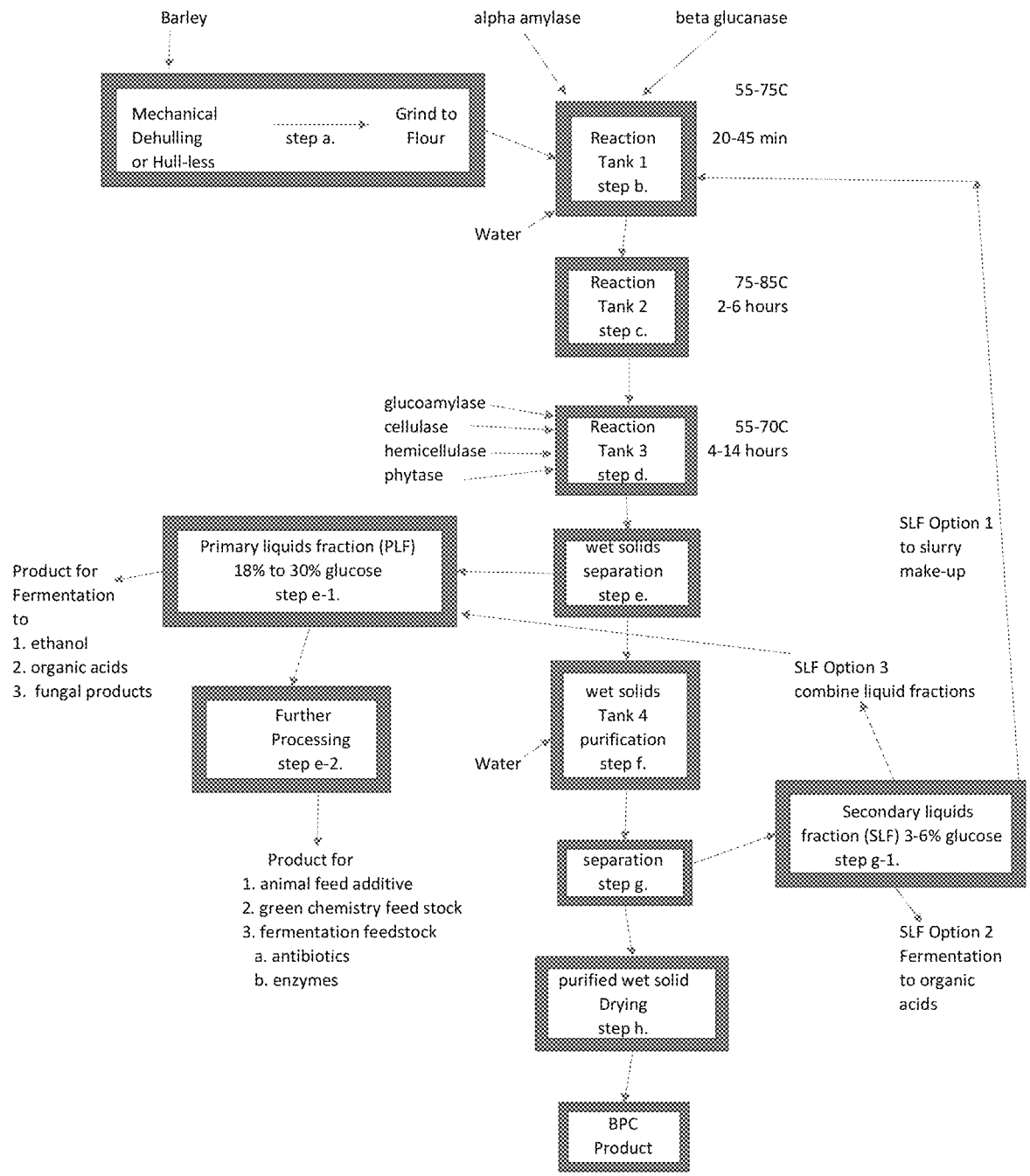
FIG. 2 illustrates a process flow according to the present invention used to create the claimed barley protein concentrate where an additional purification step occurs in an additional reaction tank, Tank 4.
Figure 3:
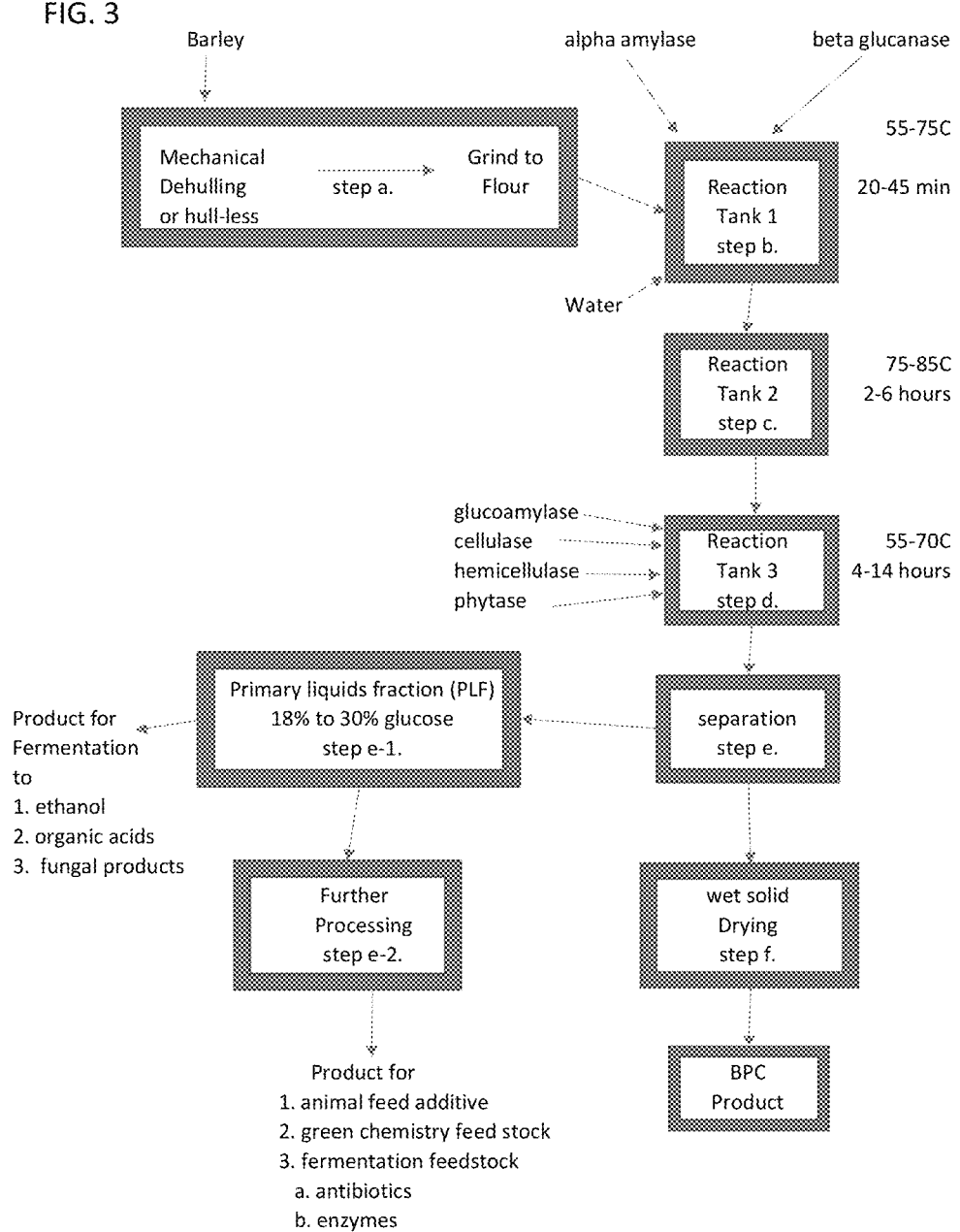
FIG. 3 illustrates a process flow according to the present invention where only one separation step is used to harvest the liquid glucose stream.
Figure 4:
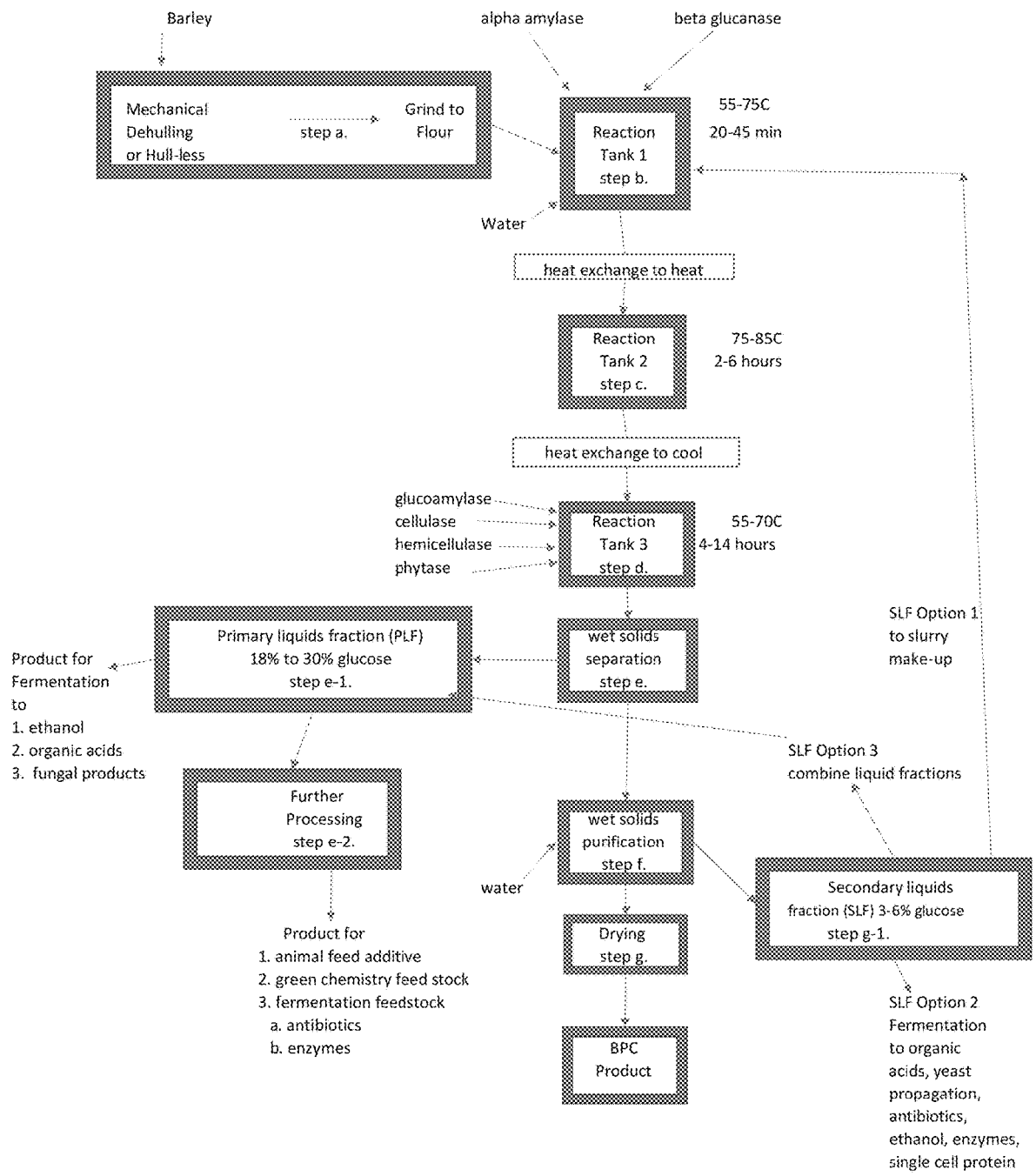
FIG. 4 illustrates the process flow according to the present invention used to create the claimed barley protein concentrate and shows heat exchange points which may be implemented such as by the use of a heat exchanger for heating and cooling between tank transfers.

Some acceptable variations in the process are reflected in FIGS. 2-4. No matter these variations, the process will not use harsh chemicals or fermentation steps or organisms to create the barley protein concentrate. At the conclusion of the process disclosed herein, the present invention's BPC product containing 65% protein is ready for use. The variation shown in FIG. 2 is that the purification step occurs by mixing the wet solid from step (e) with water into a fourth tank prior to the separation as opposed FIG. 1 which occurs through continuous flow paddle mixer.

Additional variation shown in FIG. 3 describes the process with a single separation step and without a purification stage and second separation step. Various circumstances may arise where a single separation step meets the objectives for the final protein concentrate. In one instance, the barley protein concentrate and separation of liquids and solids may only occur once if the glucose levels in the final product solid are already below 1%. Such a circumstance may arise where a superior centrifuge in the separation in step (e) can reduce the glucose in the final BPC to less than 1%, or an otherwise acceptable level. This embodiment of the present invention may also be desirable if the objectives for the final BPC product permit or allow for inclusion of five (5%) or more of sugars.

Example: Rotating Filter for Purification Step

In one preferred implementation of the present invention, Barley is processed for production of barley protein concentrate according to the steps in the flow diagram in FIG. 4 with the added benefit of a heat exchanger located between and assisting in temperature increases and decreases for steps (b)-(d). Barley is mixed with hot water in step (b), see reaction tank 1, to achieve a slurry of 35% solids and 65% liquid. The barley slurry is processed with temperature, enzyme additions and hold times within the parameters of steps (b) through (d). For the separation of the purified solids in step (e), a continuous flow rotary screen with counter-current flow of water is used. The particular equipment tested was a "Nessie" marketed by the Ziemann Holvrieka company in Germany. The Nessie test model for potential BPC purification was fitted with two rotary screens operated in series. Commercial units may have up to 4 rotary screens operated in series. The Nessie may serve as an alternative to centrifuges for the separation and purification steps.

During this Nessie test, at step (e), the primary liquids fraction contained 22.8% glucose. Then, when employing the Nessie during the step (f) purification stage of the test, wet solids from step (e) were mixed with an equal volume of water at 65° C. in a stirred tank. The mixture was then pumped to the inlet of the first rotary filter. Samples of feed slurry were pumped to the Nessie, then the secondary liquids fraction from the discharge of the first rotary screen and the second rotary screen were collected and assayed for glucose concentration and dry weight of recovered solids. The test results showed the following:

| Sample | Glucose % | Solids % |
| --- | --- | --- |
| Feed | 5.7 | 26.5 |
| Wheel filter 1 | 2.4 | 26.7 |
| Wheel filter 2 | 0.8 | 22.4 |

Using the rotary disc filter, the test results show that the glucose concentration in the secondary liquids fraction is within the range of the secondary liquids fraction obtained from using a centrifuge as the equipment for separation in step (e) or (f). Final glucose concentration in the recovered BPC is within the desirable range for the present invention—that being less than 1%. In this test, the final amount of glucose concentration within the BPC was approximately 0.78%.

Referring to FIGS. 2-4, the primary liquids fraction containing glucose created during the BPC process can be transferred directly to fermentation processes such as to make ethanol or other fermentation products, see step (e-1). In an additional aspect of the invention, the primary liquids fraction is further processed, see step (e-2) to remove soluble protein and other impurities using ion exchange, filtration, precipitation or other known methods for removing suspended solids, soluble protein and other impurities. The primary liquids fraction may be concentrated using standard known evaporation equipment to facilitate transportation and stabilizes the glucose solution from microbial degradation. FIGS. 2 and 4 also show the recovered secondary liquid fraction of step (g-1) which can be recycled or used as discussed further herein.

Example: Separation Step Before Saccharification

Figure 5:
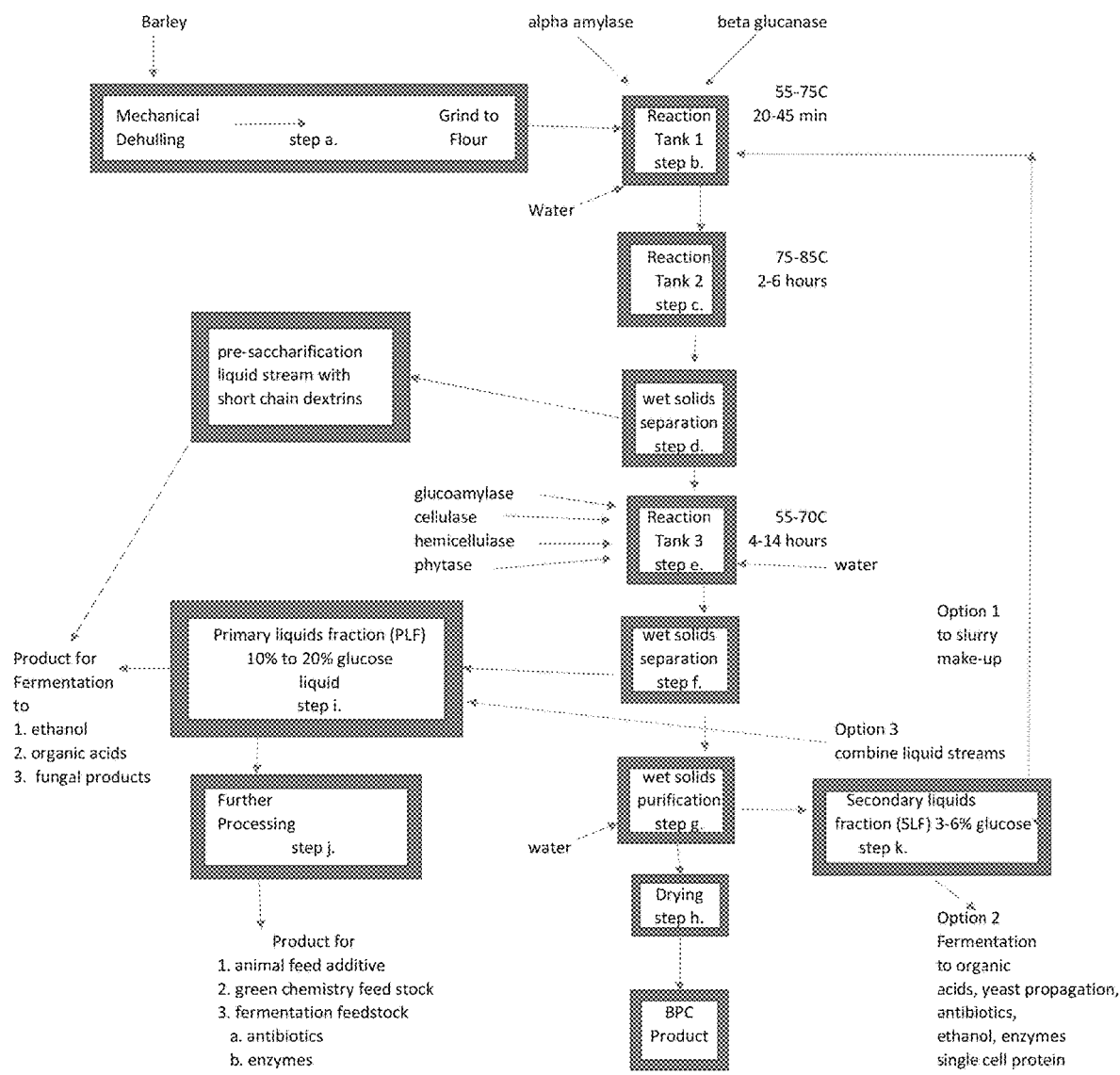
FIG. 5 illustrates an embodiment of the present invention where short chain dextrins are separated prior to the saccharification step.

As shown in FIG. 5, another embodiment solids liquid separation occurs after reaction tank 2 but before saccharification. A pre-saccharification liquid stream of short chain dextrins is separated from the slurry by centrifuge (step "d"). Then, as indicated at step "e", the wet solids fraction is resuspended in water and treated with glucoamylase, cellulase, hemicellulase and phytase then separated (step "f") again to recover the primary liquids fraction (step "i") which may also contain additional soluble dextrins. The wet solids from step "f" are then purified as in step "g" with addition of water to remove residual soluble sugars. The pre-saccharification liquids fraction and primary liquids fraction both containing soluble dextrin are intended as feedstock for fermentation. The exemplary implementation illustrated in FIG. 5 for producing a barley protein concentrate allows modifications to the process and may comprise the following steps:

(a) dehulling the barley to remove hard exterior hull to reduce fiber but not too much that you lose protein; using hammer mill for grinding barley to produce a barley flour;

(b) mixing the barley flour with hot water at a temperature of 55° C. to 75° C. to form a slurry in a mix tank (reaction tank 1); adding thermotolerant enzymes, and holding the modified slurry containing enzymes to allow a reaction time of 20 to 45 minutes; and (c) transferring the modified slurry to reaction tank 2 heated by steam thereby increasing the modified slurry temperature to 75° C. to 85° C. and allowing a reaction time of 2 to 6 hours;

(d) centrifuging the modified slurry to separate pre-saccharification liquid stream with short chain dextrins;

(e) transferring pre-saccharification solid to reaction tank 3, adding water, cooling the modified slurry to 55° C. to 70° C. and adding enzyme preparations with carbohydrate hydrolytic activities and phytase and allowing a reaction time of 4 to 12 hours;

(f) separating the modified slurry into a solids fraction and a primary liquids fraction;

(g) further purifying (wash/dilution) the barley protein concentrate and separating a purified solids fraction and a secondary liquids fraction;

(h) drying the purified solids fraction from step (g) at a temperature and under conditions which do not damage or adversely affect protein, thereby producing a protein concentrate containing greater than 54% protein;

(i) recovering the primary liquids fraction containing glucose of step (f); and (j) processing the primary liquids fraction containing glucose of step (i) to an enriched form suitable for use as feedstocks for fermentation processes, livestock feeds or biochemical conversion processes.

(k) utilizing the secondary liquids stream of step (g) for various applications such as including: (1) make up water for slurry; (2) fermentation for various applications; or (3) combination with primary liquid stream for further processing.

Process Comparison, Separation of Solids Before or After Step d Saccharification For this comparative analysis, a slurry of 25% weight per weight (w/w) was created from dehulled and hammermilled barley of the variety Metcalf.

A test was conducted comparing results with solids separation after the saccharification step "d" in Reaction Tank 3 of FIG. 1 versus before step "e" of FIG. 5. Both were conducted with 25% solids loading, 300 grams milled barley mixed in 900 ml water with stirring. Enzymes, alpha amylase (Spezyme FRED) and beta glucanase, (Optimash TBG) added and slurry was heated to 82° C. and held at this temperature with continuous stirring for 4 hours. In both process options, all enzymes from Dupont Corporation and used at equal rates between the two treatments.

1. Solids Liquid Separation Before Saccharification

For the solids liquid separation before step "e" of FIG. 5, the slurry was cooled from 82° C. to about 40° C. and centrifuged 3,500×g for 10 minutes. The solids were resuspended 3:1 water to wet solids. The centrate, pre-saccharification, liquids fraction containing primarily soluble dextrins was assayed by High-performance liquid chromatography (HPLC). Enzymes from DuPont Corporation of the following varieties were added to the resuspended solids: glucoamylase (Distillase® VHP glucoamylase containing added debranching activity), and mixed cellulase, hemicellulase (Viscamyl Flow). The slurry was held overnight at 62° C. to covert residual dextrins to glucose.

2. Solids Liquid Separation After Step d Saccharification

For the solids liquid separation after step "d" such as shown in FIGS. 1-4, the slurry was cooled from 82° C. to 62° C. Enzymes of the following varieties were added to the slurry: glucoamylase (Distillase® VHP glucoamylase containing added debranching activity), and mixed cellulase hemicellulase (Viscamyl Flow). The slurry was held overnight at 62° C. with stirring. The slurry was then cooled and centrifuged, 3,500×g for 10 minutes. The primary liquids fraction was analyzed for glucose concentration. In this implementation of the test, an additional purification step "f" was conducted such as that illustrated in FIG. 1. The wet solids were resuspended 3:1 water to wet solids w/w and then separated by centrifuge again to remove residual glucose in the secondary liquids fraction.

The solids fraction was dried and assayed for protein concentration and residual glucose concentration in dry BPC solids. In both process options maximum protein concentration in final BPC of about 61% was obtained after the purification step with residual glucose of less than 1% (<10 mg/ml).

| SAMPLE | Protein % |
| --- | --- |
| Separation before saccharification | 61.09 |
| Separation after saccharification | 60.83 |

Example: Reaction Tank Options

Figure 6:
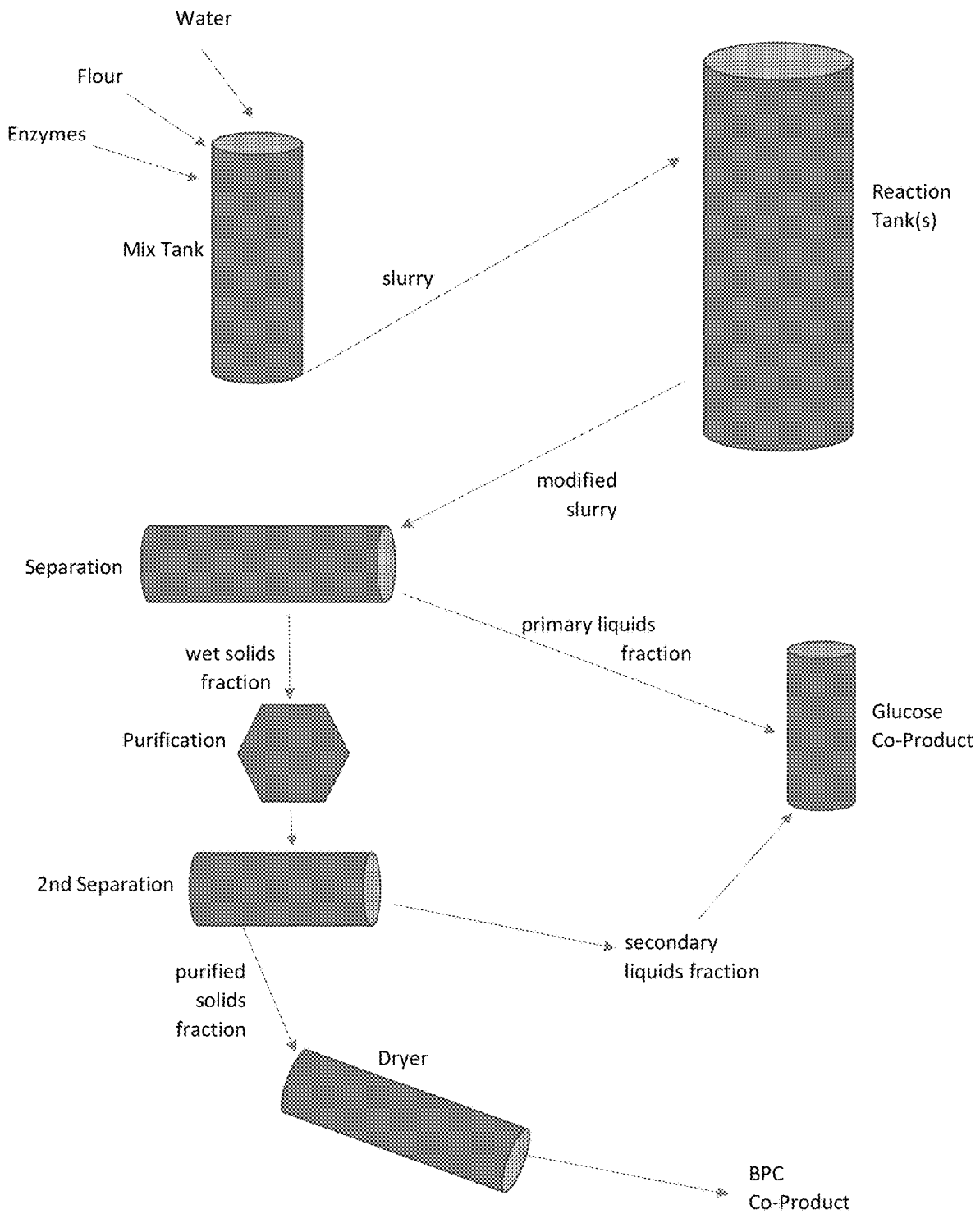
FIG. 6 is a schematic representation of the barley protein production process using only two vessels.

As illustrated in FIG. 6, a single reaction tank could house the liquefaction and saccharification steps of the present invention. In some circumstances it may be advantageous to hold the slurry in a single tank with temperature adjusted and enzymes added as it undergoes solubilization, liquefaction, and saccharification in which case at least these initial steps of the process may occur in one tank.

Example: Pilot Plant Water Wash Purification Step

Figure 7:
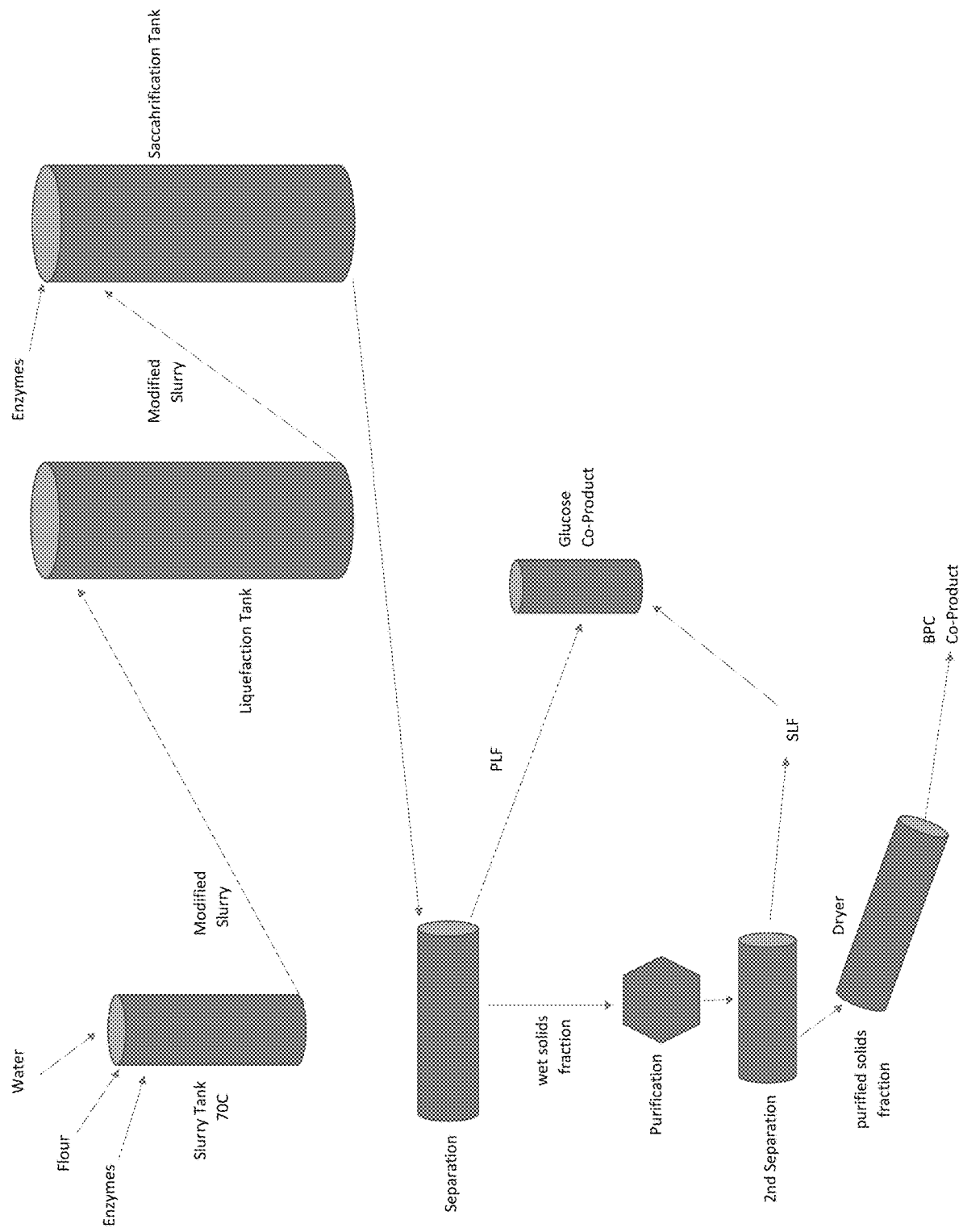
FIG. 7 is a schematic representation of the barley protein process producing glucose and barley protein concentrate co-products.

FIG. 7 schematically represents an exemplary pilot plant implementation of the present invention with three separate tanks and a purification step which is implemented through a water wash, dilution and resuspension prior to another separation step prior to drying of the solids fraction. One test run of a pilot plant process such as that represented in FIG. 7 was implemented as follows: 830 lbs of flour were added with 1,937 lbs of water and enzyme to mix tank. The resulting slurry was held at 70° C. for 45 minutes while the mix tank was agitated. The slurry was heated to at 82° C. such as by pumping through a jet cooker pipe into the liquefaction tank, tank 2. The liquefaction tank was agitated for 6 hours with the tank remaining between 80° C. and 82° C. After 6 hours, the slurry was moved to the saccharification tank, tank 3, and was cooled to 65° C. and enzymes were added to tank 3. The slurry was held for 12 hours between 60° C. and 65° C. while being agitated. After 12 hours, the slurry was pumped through a decanter centrifuge. The centrate from the centrifuge, containing glucose, was collected and pumped to a holding tank for co-product utilization. The wet solids from the centrifuge were collected and in the purification step, mixed with water at three weights of water to one weight of wet solids. The slurry of wet solids and water were agitated for 6.5 hours at 65° C. The temperature of the purification tank was maintained using a constant recycle loop through a pump and steam jet cooker. After 6.5 hours, the slurry was pumped through a decanter centrifuge, the wet solids were transported to a microwave dryer and dried to 6.2% moisture. The dried solids measured 61.5% protein at 6.2% moisture.

Further Processing to Increase Protein Concentration

In laboratory tests of primary separation with a centrifuge, solids showed distinctive layers of varying density and particle size. Separating and analyzing these different layers showed that the most dense and larger particles in the bottom layer contained low protein concentration, most of the protein occurred in the less dense or mid and top layers. By separating out the more dense and larger particles, a protein concentrate could be produced from the less dense layers which contained more than 70% protein. Separation of the low protein, high density solids from solids with higher protein concentration can occur at different steps in the process.

Flour screen: Instead of waiting until the separation or purification steps, protein concentration was also found to be optimizable by screening flour after grinding and before mixing flour with water in reaction tank 1. The screening of the flour removes residual hull and larger insoluble particles. When this additional purification stage is added to the process, the prescreened flour is used in the place of flour in the process as described. Adding this prescreening steps will increase the protein concentration. When using flour prescreening, alone and without the other concentration-optimization purification steps, protein concentration in the dry solids may be as high as 72%.

Filtration fractionation to obtain BPC with increased protein concentration: In one test, BPC was prepared by method of solids separation after saccharification except that in the purification step, wet solids were resuspended by washing through a screen, 20 mesh US standard. The slurry that passed through the screen was then centrifuged, the solids dried and the secondary liquid fraction sent to further processing. The final protein concentration of screened dried BPC was 71%.

Centrifuge fractionation to obtain BPC with increased protein concentration: In another test, BPC was prepared by methods described in the filtration example (above using process options of solids separation before or after saccharification, except that wet solids recovered in final centrifuge of purification were split into two fractions: Bottom, or dense and Top, or less dense. Fractions were dried separately and assayed for protein concentration. Protein concentration in the top fraction was 67% to over 68%. Protein distributes in less dense fraction enabling production of BPC with significantly higher protein concentration.

| | Protein % |
| --- | --- |
| Separation before saccharification | |
| Bottom | 51.06 |
| Top | 67.01 |
| Separation after saccharification | |
| Bottom | 51.19 |
| Top | 68.69 |

Combining one or more of the above additional purification steps with other purification techniques will continue to result in higher concentration levels of protein in the final BPC.

Example: Maximizing Water Balance

Figure 8:
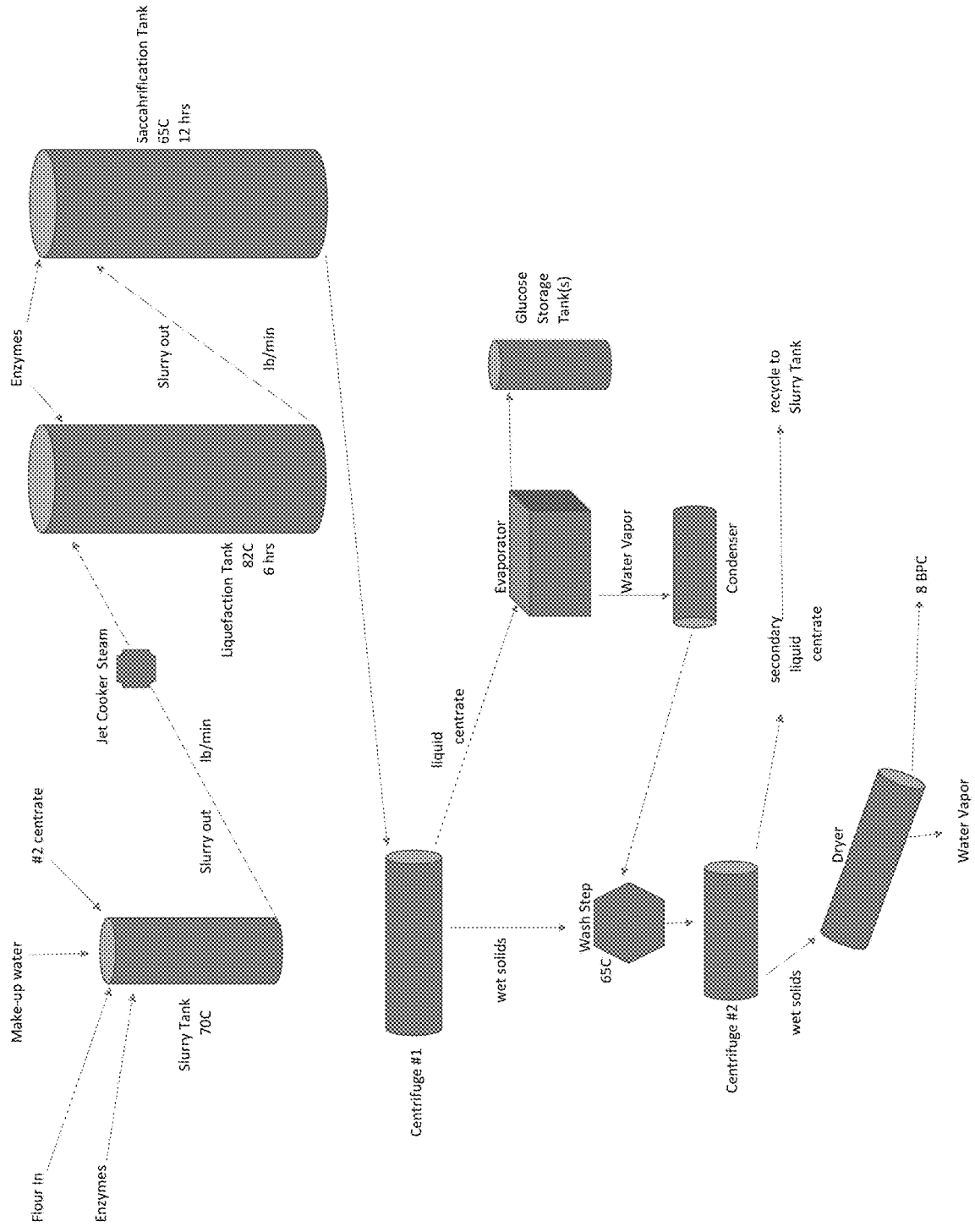
FIG. 8 is a schematic representation is one example implementation of the barley protein production process where water is recycled and reused at various stages of the process.

As illustrated in FIG. 8, one exemplary embodiment of the process for producing a barley protein concentrate comprises the following steps:
  mixing flour with hot water at a temperature of 70° C. to form a slurry in a Slurry Tank (reaction tank 1);
  adding thermotolerant enzymes to the Slurry Tank;
  holding the modified slurry optionally containing enzymes in the Slurry Tank 1 to allow a reaction time of approximately 45 minutes; and
  transferring slurry to a Liquefaction Tank (reaction tank 2) while adding water heated such as by steam from a Jet Cooker, thereby increasing the modified slurry temperature to 82° C.;

optionally adding enzyme preparations with carbohydrate hydrolytic activities and phytase to the Liquefaction Tank;

allowing a liquefaction reaction time of 6 hours;

transferring the slurry to the Saccharification Tank (reaction tank 3) while cooling the modified slurry to 65° C.

adding enzyme preparations with carbohydrate hydrolytic activities and phytase to the Saccharification Tank;

allowing a reaction time of 12 hours;

separating by centrifuge the modified slurry into a wet solids fraction and a primary liquids fraction (liquid centrate);

further purifying (wash/dilution/filter/membrane) wet solids containing the barley protein concentrate such as by a wash step where water at 65° C. is added to the BPC containing wet solids fraction whereafter centrifuge is once again used to separate a purified, wet solids fraction and a secondary liquids fraction (liquid centrate);

drying the wet solids fractions such as in a dryer at a temperature and under conditions which do not damage or adversely affect protein but which removes excess water vapor, thereby producing a protein concentrate containing greater than 54% protein;

recovering the primary liquids fraction containing glucose from centrifuge #1 and optionally pulling off additional water for recycling into the wash step by running the primary liquids fraction through an evaporator to remove additional water vapor, the water vapor being run through a condenser and then placing the water back into the BPC process at the wash step; and processing the primary liquids fraction containing glucose from centrifuge #1 to a form suitable for use as feedstocks for fermentation processes, livestock feeds or biochemical conversion processes; and optionally recycling the secondary liquids fraction from centrifuge #2 back to the Slurry Tank.

Enzymes are normally added to the slurry tank and the Saccharification Tank or Slurry Tank and Saccharification Tank. However, as demonstrated in FIG. 8 and as denoted in the methods above, some or all of the liquefaction enzymes could be added in the Liquefaction Tank as opposed to the Slurry Tank. The choice will be driven by economics of each situation.

Normally, the objective is to run as high a concentration of flour in the slurry as possible. This reduces capital and operating costs, i.e., more flour in the slurry translates to more BPC product from the same size tanks but requires less energy use in heating slurry. In the embodiment demonstrated, the target is to run 30% w/w flour in the slurry. Known varieties of barley flour typically contain 2-8% beta glucans with the average closer to 5-6%. The beta glucans make the slurry very viscous and need to be converted to less viscous compounds (soluble sugars) if the slurry concentration is going to reach 30% w/w. In the example demonstrated, the enzymes (glucoamylases) are not effective, or have very limited activity time at liquefaction temperatures (80° C. or higher), therefore the enzymes are advantageously added in the Slurry Tank where the operating temperature and pH provide optimum activity. In the example illustrated at FIG. 8, the amylase enzymes work at both Slurry Tank and Liquefaction Tank temperatures, therefore such enzymes can be added in either the Slurry Tank 1 or the Liquefaction Tank steps. Adding enzymes in the Slurry Tank in the demonstrated examples gives the enzymes a longer time to solubilize the sugars and will also reduce the number of pumps and meters required for enzyme addition later.

Implementations of the process may succeed if they are run at a lower solids loading, less flour more water. In such scenarios, all the enzymes could be added in the Liquefaction Tank step. In such situations, conversion by glucoamylases would be less, resulting in a lower protein concentration, but the loss in protein concentration at the earlier stage could be offset by later increases in the protein concentration if glucoamylase was added in the Saccharification Tank step. Because this option is running lower solids in the initial slurry, it may result in increased capital and operating costs per unit of final product.

Using the condensate from the evaporator is a water balance/water use option. It is not necessary for the process to work. Water could be supplemented or wholly introduced from another source, particularly an outside source. The wash step is one option for the purification step of the process but not the only option. Also, recycling #2 centrate (secondary liquids centrate) from the #2 centrifuge back into to the Slurry Tank 1 is an option, not a requirement. Again, these opportunities to recycle water are all done with the goal to maintain a water balance in an operating production plant. The overall goal of the water balance is to have zero water discharge and optimize and reduce water input.

The wash step and second centrifuge step 6 are only one example of possible purification steps. There are more elaborate purification steps involving more or less water addition to the wet solids from #1 centrifuge. There are options to filter or pass the wet solids through a membrane, or otherwise separate or purify the wet solids containing BPC. It is also possible to forego the purification step if the objectives for the final BPC product permit or allow for inclusion of 5% or more of sugars.

In some variations of the present invention, it may be possible to eliminate the beta glucanase in step (b) of FIGS. 1-5, but the result would require a slurry with less solids content to reduce viscosity created by beta glucans, and would yield a lower quality BPC.

In one application of the invention, the BPC is a protein ingredient incorporated into aquaculture feeds at inclusion rates up to 50%.

In another application of the invention, the BPC is a protein ingredient incorporated into feeds for livestock such as cattle, hogs, or into feeds for poultry at inclusion rates of up to 60%.

In another application of the invention, the BPC is a protein ingredient incorporated into feeds for pets including dogs, cats or other human companion animals requiring protein in feed.

In another application of the invention, the BPC is incorporated as a protein ingredient into foods for human consumption including such foods as plant based alternative protein products, milk substitutes, protein bars, cereals etc.

Figure 9:
FIG. 9 is a table showing a feed analysis report for a concentrated protein and sugar solution, such as in step (e-2), according to the methods described herein.

As illustrated in FIG. 1, the primary liquids fraction containing glucose created during the BPC process can be transferred directly to fermentation processes such as to make ethanol or other fermentation products, see step (h). In an additional aspect of the invention, the primary liquids fraction is further processed, see step (i). Glucose can be further purified in step (i) to remove soluble protein and other impurities using ion exchange, filtration, precipitation or other known methods for removing suspended solids, soluble protein and other impurities. The primary liquids fraction may be concentrated using standard known evaporation equipment. In one example, the final concentration of glucose is about 60% glucose (50% to 70%). This facilitates transportation and stabilizes the glucose solution from microbial degradation. The concentrated primary liquids fraction can be used in fermentations, in livestock feeds as an energy source, or as a feedstock for conversion to biochemicals such as organic acids or polyols. The colloidal particles and soluble proteins in the primary liquids fraction also have nutritional value; concentrating the primary liquids fraction also concentrates the protein and suspended solids which is a particular advantage when the concentrated glucose is used as a livestock feed supplement such as in dairy cattle or as a feedstock for fermentation processes where additional nutrients are advantageous. FIG. 9 is a table showing a nutritional analysis of the concentrated sugar stream from this process.

As yet another option illustrated in FIG. 1, the secondary liquid fraction glucose from the purification step (f) may be recovered—step (j)—and has processing options. In one option, the secondary liquids fraction is recycled as it is mostly water and it is useful as water combined with barley flour to form the slurry in the first reaction tank, step (b).

Alternatively, as illustrated in FIG. 1, in a second option the secondary liquids fraction from the purification step (f) is combined with the primary liquids fraction recovered from the first solid liquid separation in step (e).

The glucose streams that are produced from the claimed process may be commercialized and sold to other companies as a feedstock for other processes. Some industries may find that by adding a selected microbe such as yeast, *Rhizopus* sp. or *Lactobacillus* sp., can be added to inoculate the sugar co-products of the primary or secondary liquid fractions in order to feed fermentation processes to produce ethanol or organic acids in systems outside of the production of the barley protein concentrate. The organic acids that may be useful include lactic acid, malic, or fumaric acid.

The glucose streams produced from the claimed process may be further useful for other purposes. Some industries may find advantages to using the sugar co-products of the various sugar streams of the present invention useful in substrates for selected microbes. In still further utilizations of the sugar co-products, products may be produced for feedstock for multiple processes and products. By way of example and not limitation, examples of uses for the co-products of the process include: animal feed additives, substrates for green chemistry, or fermentation feedstock for antibiotic or enzyme development. In some cases, the secondary liquids fraction may be used in fermentation to organic acids, cell mass or other fermentation products, yeast propagation, antibiotics, ethanol, enzymes, or single cell protein development.

To minimize waste of the claimed process, byproducts are utilized whenever possible. Examples have been given for recycling water and reusing heat. Additional examples include, using the barley hulls produced from dehulling in the first process stages are used as livestock feed. The barley hulls produced from dehulling are used as a feedstock for processes to produce purified fiber products. Alternatively, the barley hulls produced from dehulling are used as fuel for generating process energy such as steam.

It is further intended that any other embodiments of the present invention which result from any changes in application or method of use or operation, method of manufacture, shape, size, or material which are not specified within the detailed written description or illustrations contained herein, yet are considered apparent or obvious to one skilled in the art, are within the scope of the present invention.

What is claimed is:

1. A process for producing a barley protein concentrate and sugar co-products from barley flour obtained from dry-milling barley grain, the process comprising:

a solubilization step wherein the dry-milled barley flour is mixed with hot water and thermotolerant carbohydrate hydrolytic enzyme preparations to make a slurry containing solubilized carbohydrates, a liquefaction step wherein the slurry is heated and held for a period sufficient to gelatinize starch granules and solubilize starch to create a modified slurry, a saccharification step wherein the modified slurry is cooled, mixed with carbohydrate hydrolytic enzyme preparations and held for a period sufficient to hydrolyze starch dextrins, cellulose and hemicellulose to sugars, at least one separation step wherein the modified slurry is separated into a wet solids fraction and a primary liquid sugars fraction, and a protein concentration step wherein residual sugars in the wet solids fraction are removed as a secondary liquid sugars fraction, a drying step occurring at a temperature and under conditions which do not damage or adversely affect protein structures, thereby producing the barley protein concentrate with protein concentration 4-6 fold greater than the barley flour and the sugar co-products of the primary liquid sugars fraction and the secondary liquid sugars fraction, wherein an elapsed time for the process is less than 24 hours.

2. The process of claim 1, wherein the barley protein concentrate contains greater than 54% protein.

3. The process of claim 1, wherein the carbohydrate hydrolytic enzyme preparations are selected from a group consisting of alpha amylase, glucoamylase, pullulanase, cellulase, and hemicellulase.

4. The process of claim 1, wherein the sugars created in the saccharification step result in a sugar solution wherein more than 90% of the sugars are glucose.

5. The process of claim 1, wherein no fermentation occurs in the process for producing barley protein concentrate.

6. The process of claim 1, wherein:

the water used in the solubilization step is hot water at a temperature of approximately 55° C. to 75° C., and the thermotolerant carbohydrate hydrolytic enzyme preparations alpha amylase and beta glucanase are mixed with the slurry and held for a reaction time of approximately 20 minutes to 45 minutes, the slurry is heated to approximately 75° C. to 85° C. through the liquefaction step, and the period sufficient to gelatinize starch granules and solubilize starch to create the modified slurry is approximately 2 to 6 hours, the modified slurry is cooled to between approximately 55° C. to 70° C. through the saccharification step, and mixed with the carbohydrate hydrolytic enzyme preparations containing glucoamylase, pullulanase, cellulase, and hemicellulase, and held for the period of approximately 4 to 14 hours, a purified solids fraction created through the protein concentration step after removal of the secondary liquid sugars fraction is dried during the drying step such that, the barley protein concentrate contains greater than 54% protein, and the primary liquid sugars fraction, and the secondary liquid sugars fraction are suitable for use as sweeteners, feedstocks for fermentation processes, livestock feeds, or biochemical conversion processes.

7. The process of claim 6, wherein an enzyme preparation phytase is added during the saccharification step.

8. The process of claim 6, wherein the protein concentration step occurs with the performance of at least one of a group of steps consisting of:
- one or more water dilution wash steps,
- one or more filtering steps, and
- one or more additional solids-liquids separation steps.

9. The process of claim 6, wherein the process further comprises the steps of recycling water produced in the process for use in other steps of the process.

10. The process of claim 6, wherein no fermentation occurs in the production of the barley protein concentrate.

11. The process of claim 1, wherein one sugar stream containing short chain soluble dextrins is produced from the process before the saccharification step.

12. The process of claim 1, wherein the process increases protein concentration of the barley feedstock by approximately 400% to 600%.

13. The process of claim 1, wherein the barley flour starts with 10%-15% protein concentration and ends with the barley protein concentrate having greater than 54% protein concentration.

14. The process of claim 1, wherein the primary liquids sugars fraction contains greater than 18% glucose.

15. The process of claim 1, wherein the primary liquids fraction contains approximately 23% glucose.

16. The process of claim 1, wherein no organisms are employed.

* * * * *